(12) United States Patent
Sinclair (10) Patent No.: US 9,131,848 B2
(45) Date of Patent: Sep. 15, 2015

(54) ABERRATION CORRECTED SHORT WORKING DISTANCE OPTICAL PROBE WITH LARGE CONFOCAL PARAMETER

(71) Applicant: NinePoint Medical, Inc., Cambridge, MA (US)

(72) Inventor: Matthew A. Sinclair, Somerville, MA (US)

(73) Assignee: NINEPOINT MEDICAL, INC., Cambridge, MA (US)

( * ) Notice: Subject to any disclaimer, the term of this patent is extended or adjusted under 35 U.S.C. 154(b) by 54 days.

(21) Appl. No.: 13/956,698

(22) Filed: Aug. 1, 2013

(65) Prior Publication Data

US 2014/0037245 A1     Feb. 6, 2014

Related U.S. Application Data

(60) Provisional application No. 61/678,761, filed on Aug. 2, 2012.

(51) Int. Cl.
| | | |
|---|---|---|
| *G02B 6/32* | (2006.01) | |
| *A61B 5/00* | (2006.01) | |
| *G02B 6/34* | (2006.01) | |
| *G02B 6/36* | (2006.01) | |
| *G02B 6/26* | (2006.01) | |

(52) U.S. Cl.
CPC ............. *A61B 5/0082* (2013.01); *A61B 5/0066* (2013.01); *A61B 5/0084* (2013.01); *G02B 6/32* (2013.01); *G02B 6/34* (2013.01); *A61B 2562/16* (2013.01); *G02B 6/262* (2013.01); *G02B 6/3624* (2013.01)

(58) Field of Classification Search
CPC ...... G02B 6/32; G02B 6/4206; G02B 6/4204; G02B 6/4214; G02B 6/4246; G02B 6/4292
USPC .......................................... 385/15, 31, 33, 36
See application file for complete search history.

(56) References Cited

U.S. PATENT DOCUMENTS

| | | | |
|---|---|---|---|
| 5,817,015 A | 10/1998 | Adair | |
| 2003/0016452 A1 | 1/2003 | Sayag | |
| 2003/0133219 A1* | 7/2003 | Ishizuka et al. | 360/77.03 |
| 2006/0067620 A1 | 3/2006 | Shishkov et al. | |
| 2008/0228033 A1 | 9/2008 | Tumlinson et al. | |
| 2013/0107274 A1* | 5/2013 | Vertikov et al. | 356/479 |

OTHER PUBLICATIONS

International Search Report and Written Opinion dated Jan. 15, 2014 on Application No. PCT/US2013/053196 filed Aug. 1, 2013 as issued by the International Search Authority.

* cited by examiner

*Primary Examiner* — Jennifer Doan
(74) *Attorney, Agent, or Firm* — Sorell, Lenna & Schmidt, LLP (57) ABSTRACT

An optical probe is provided. The optical probe includes a lens extending along an axis between a first end and a second end. A spacer extends along the axis between a first end and a second end. The first end of the spacer is connected to the second end of the lens. A prism is connected to the second end of the spacer such that the prism is spaced apart from the lens by the spacer.

20 Claims, 8 Drawing Sheets

ABERRATION CORRECTED SHORT WORKING DISTANCE OPTICAL PROBE WITH LARGE CONFOCAL PARAMETER

TECHNICAL FIELD

The present disclosure generally relates to medical devices, systems and methods for imaging in biomedical and other medical and non-medical applications, and more particularly, to optical probes for Optical Coherence Tomography (OCT) imaging where a short working distance is needed with a large confocal parameter to image deep into tissue.

BACKGROUND

Various forms of imaging systems are used in healthcare to produce images of a patient. Often, an image of an internal cavity of a patient is required. These cavities can include areas of the digestive system or the respiratory system. When imaging tissue features of these systems, fiber optic endoscopy is often utilized.

One type of fiber optic probe used in an endoscope is based on Optical Coherence Tomography (OCT) techniques. OCT provides structural information on tissue with high resolution. OCT can provide this information in real time and in a non-invasive manner. Many different lens types have been used to construct fiber optic probes. These lenses include fiber lenses, ball lenses and Gradient Index (GRIN) lenses. Lens materials can vary from glass to plastic to silicon.

Figure 1:
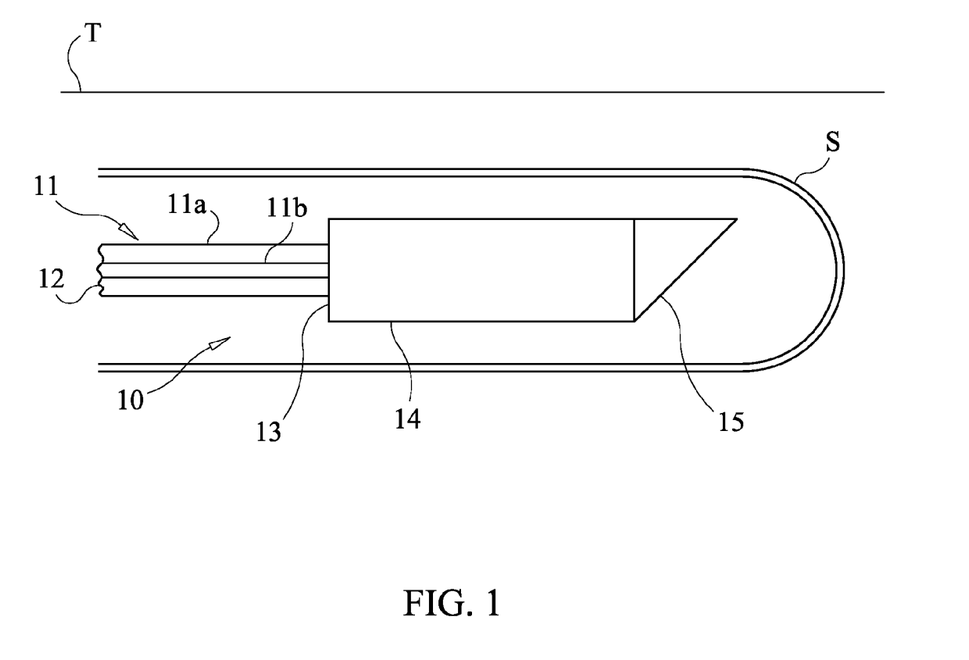
FIG. 1 is a side, cross-sectional view of a conventional optical probe using a gradient index lens.

As shown in FIG. 1, one type of OCT probe 10 is comprised of an optical fiber 11 having a casing 11a, a fiber core 11b, a proximal end 12 and a distal end 13, a GRIN lens 14 connected directly to distal end 13 of the optical fiber 11, and a prism 15 connected directly to GRIN lens 14 and configured to deflect light into surrounding tissue T. Probe 10 is typically connected to a coherent light source at proximal end 12 of optical fiber 11. Probe 10 is typically contained within a sheath S. Sheath S containing probe 10 is inserted into a cavity of a patient to image into tissue T surrounding probe 10. Sheath S protects probe 10 and tissue T from damage. Fiber core 11b, GRIN lens 14 and prism 15 are typically connected by fusing the components together or using an epoxy to glue the components together.

An optical probe must be specifically manufactured to conform to optical parameters required for a specific use. Esophageal imaging requires probes of specific design to properly image into surrounding tissue. Typical prior art probes do not provide the specific optical operating parameters required in esophageal imaging. This disclosure describes an improvement over these prior art technologies.

SUMMARY

Accordingly, an optical probe is provided which includes a lens extending along an axis between a first end and a second end. A spacer extends along the axis between a first end and a second end. The first end of the spacer is connected directly to the second end of the lens. A prism is connected directly to the second end of the spacer such that the prism is spaced apart from the lens by the spacer.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure.

Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "superior" and "inferior" are relative and used only in the context to the other, and are not necessarily "upper" and "lower".

Reference will now be made in detail to the exemplary embodiments of the present disclosure, which are illustrated in the accompanying figures.

Figure 2:
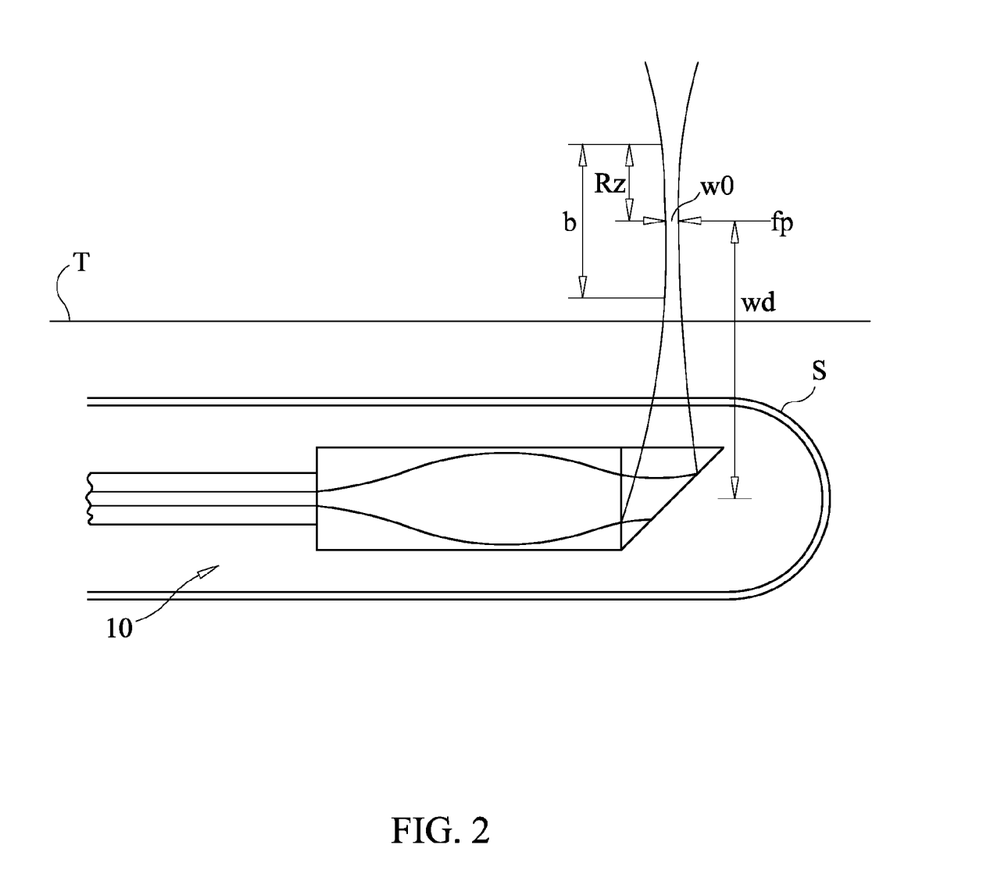
FIG. 2 is a side, cross-sectional view illustrating various operating parameters of an optical probe.

Proper imaging into tissue using an OCT probe requires strict compliance to probe specifications in order to precisely set the optical parameters in a manner that is effective for esophageal imaging. These parameters can include the Rayleigh Range $R_z$, the confocal parameter b, the waist w, the focal point fp, and the working distance wd. In some embodiments, the parameters include the focal length fl. The term "beam waist" or "waist" as used herein refers to a location along a beam where the beam radius is a local minimum and where the wavefront of the beam is planar over a substantial length (i.e., a confocal length). The term "working distance" as used herein means the distance between the optical axis of the fiber and the waist w.

As stated above, an optical probe must be specifically manufactured to conform to the optical parameters required for effective esophageal imaging. Indeed, esophageal imaging requires probes of specific design to properly image into surrounding tissue T. When using an optical probe without a balloon for esophageal imaging, a short working distance with large confocal parameter is required. In esophageal imaging there is generally about a 1 millimeter (mm) distance between an outer surface of sheath S and tissue T. In attempts to manufacture an optical probe that conforms to these parameters, several designs have been utilized.

One design utilizes a ball lens. A ball lens is difficult to manufacture with little control and correction over aberrations caused by sheaths covering the optical probe. Another design uses a GRIN lens. Unfortunately, the particular GRIN lens/fiber with a significantly greater index of refraction gradient is costly to manufacture with extremely tight tolerances due to the fast gradient index change. Another design utilizes an outer balloon structure to increase the working distance. However, the use of a balloon often deforms the surrounding tissue and also flattens the natural surface features.

Detailed experimentation conducted by the inventor of the present disclosure has produced an optical probe that conforms to the specific requirements of esophageal imaging. Certain aspects of the inventor's experimentation will now be discussed.

Figure 3:
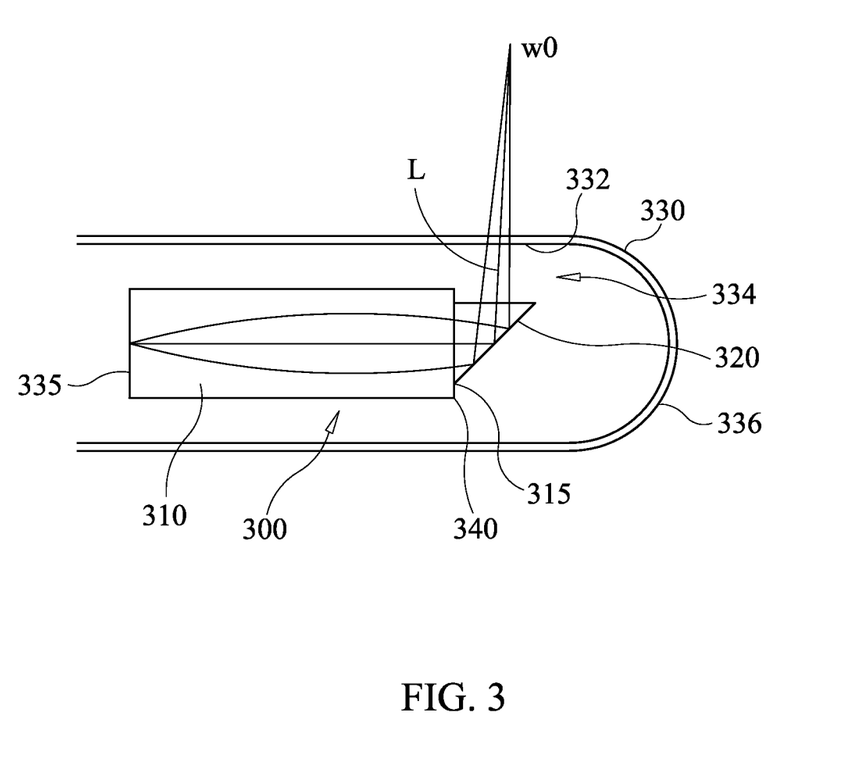
FIG. 3 is a side, cross-sectional view of an optical probe having a lens and a prism.

FIG. 3 illustrates an optical probe 300 having a GRIN lens 310 directly connected to a prism 320 using epoxy 315. One or more optical fibers (not shown) would be connected to the end of GRIN lens 310. The optical fiber(s) may be connected to a light source. A sheath 330 is also illustrated in FIG. 3. Sheath 330 includes an inner surface 332 defining a passageway 334 having lens 310 and prism 320 removably disposed therein. An end 336 of sheath 330 defines a blunt tip.

Table 1A lists the specifications of the components of optical probe 300. As shown in Table 1A, GRIN lens 310 has a thickness of 3.2810 mm defined by the distance between an end 335 of lens 310 and an opposite end 340 of lens 310. Table 1B lists the resulting beam characteristics of probe 300. As shown in Table 1B, the configuration of probe 300 of FIG. 3 results in a long working distance and a very small waist. Although this results in an acceptable Rayleigh Range Rz of 0.408 mm, the long working distance is unacceptable since the area in focus is to far away from the probe. The area in focus is the confocal parameter centered around the waist.

In attempts to correct for aberration and adjust the optical parameters, the use of a spacer placed between the optical fiber(s) and the lens has been attempted. Indeed, the variance of the spacer is an important factor for determining the waist and the working distance of a probe because as a spacer length increases, the waist becomes smaller and the working distance becomes shorter.

Figure 4:
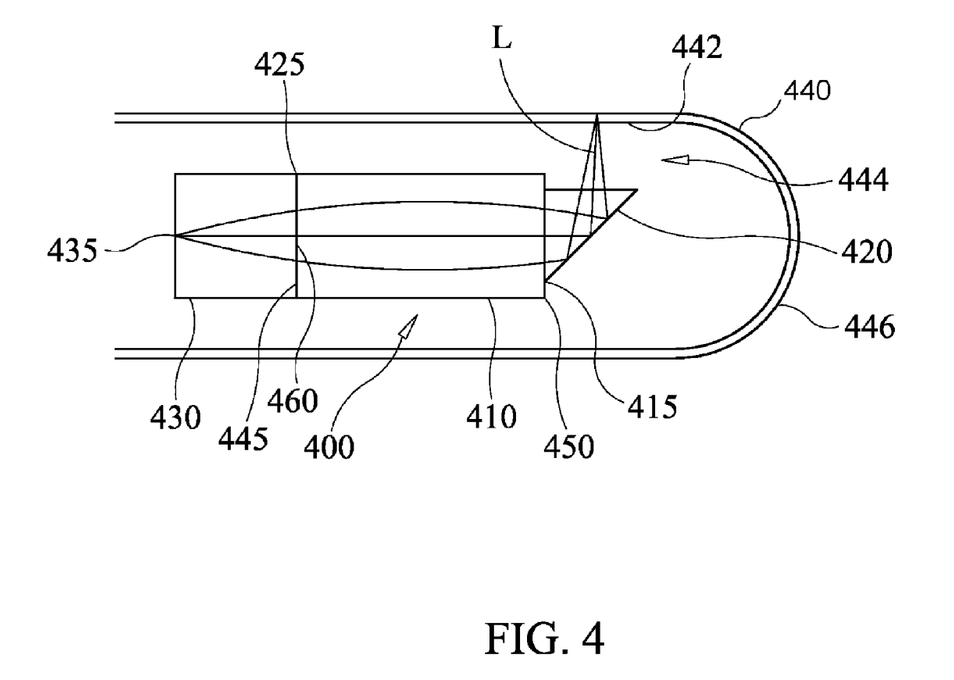
FIG. 4 is a side, cross-sectional view of an optical probe having a spacer, a lens and a prism.

FIG. 4 illustrates an optical probe 400 having a GRIN lens 410 directly connected to a prism 420 using epoxy 415. Positioned prior to GRIN lens 410 is a spacer 430, and connected thereto also using an epoxy 425. One or more optical fibers (not shown) would be connected to an end 435 of spacer 430. A sheath 440 is also illustrated in FIG. 4. Sheath 440 includes an inner surface 442 defining a passageway 444 having lens 410, prism 420 and spacer 430 removably disposed therein. An end 446 of sheath 440 defines a blunt tip.

Table 2A lists the specifications of the components of optical probe 400. As shown in Table 2A, GRIN lens 410 has a thickness of 3.0000 mm defined by the distance between an end 445 of lens 410 and an opposite end 450 of lens 410 and spacer 430 has a thickness of 1.000 mm defined by the distance between end 455 and an opposite end 460 of spacer 430.

As shown in FIG. 4, end 445 directly engages end 460 and end 455 is positioned opposite end 450. Table 2B lists the resulting beam characteristics of probe 400. As shown in Table 2B, the configuration of probe 400 of FIG. 4 results in a very short focal length and thus a very short working distance and a very small waist. The resulting unacceptable Rayleigh Range Rz is approximately 0.06 mm.

Figure 5:
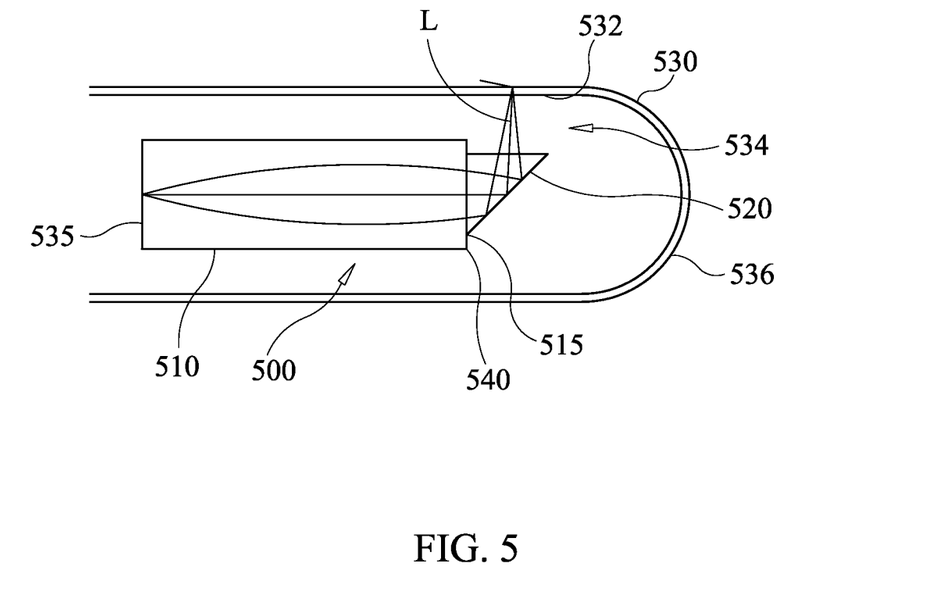
FIG. 5 is a side, cross-sectional view of an optical probe having an elongated lens and a prism.

Another attempt was made to adjust the optical parameters into proper working ranges. FIG. 5 illustrates an optical probe 500 having a GRIN lens 510 directly connected to a prism 520 using epoxy 515. One or more optical fibers (not shown) would be connected to an end 535 of GRIN lens 510. A sheath 530 is also illustrated in FIG. 5. Sheath 530 includes an inner surface 532 defining a passageway 534 having lens 510 and prism 520 removably disposed therein. An end 536 of sheath 530 defines a blunt tip.

Table 3A lists the specifications of the components of optical probe 500. As shown in Table 3A, GRIN lens 510 has a thickness of 3.9200 mm defined by the distance between end 535 an opposite end 540 of lens 510. Table 3B lists the resulting beam characteristics of probe 500. As shown in Table 3B, the configuration of probe 500 of FIG. 5 results in a very short focal length and thus a very short working distance and a very small waist. The resulting unacceptable Rayleigh Range Rz is approximately 0.1 mm.

Figure 6:
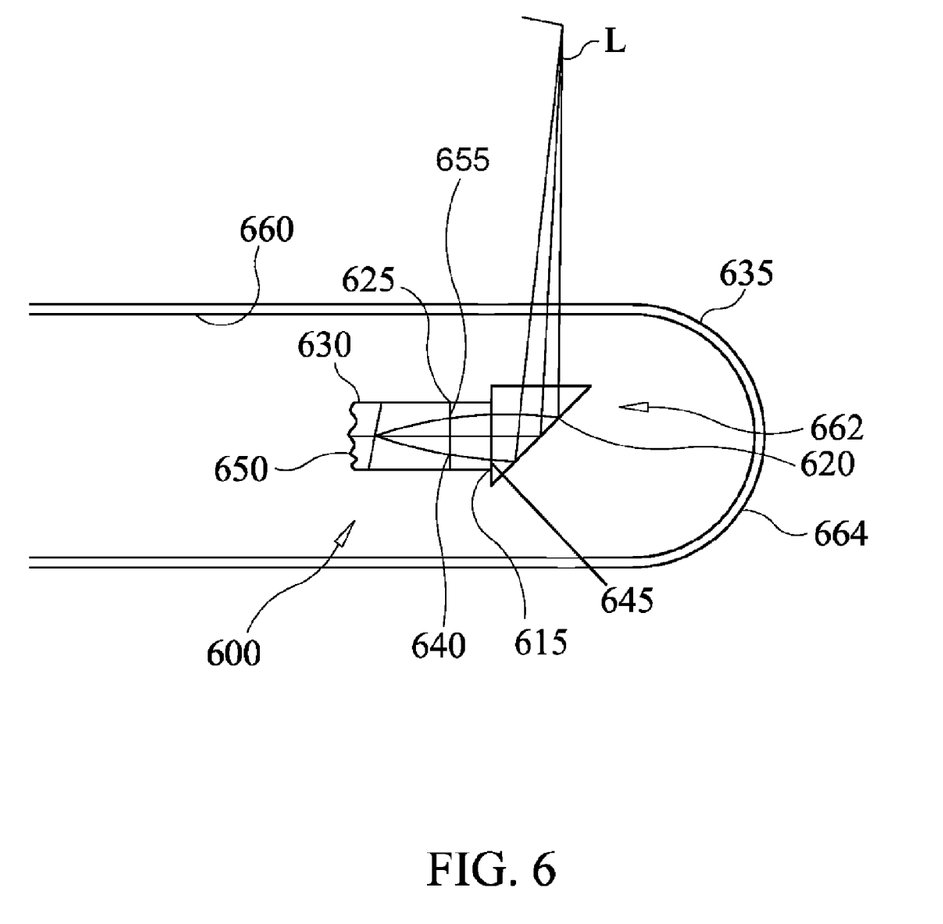
FIG. 6 is a side, cross-sectional view of an optical probe having a large spacer, a small lens and a prism.

A further attempt was made to adjust the optical parameters into proper working ranges. FIG. 6 illustrates an optical probe 600 having a GRIN lens 610 connected directly to a prism 620 using epoxy 615. Positioned prior to GRIN lens 610 is spacer 630, and connected thereto also using an epoxy 625 or fusion spliced. One or more optical fibers (not shown) would be connected to an end 650 of spacer 630. A sheath 635 is also illustrated in FIG. 6. Sheath 635 includes an inner surface 660 defining a passageway 662 having lens 610, prism 620 and spacer 630 removably disposed therein. An end 664 of sheath 635 defines a blunt tip.

Table 4A lists the specifications of the components of optical probe 600. As shown in Table 4A, GRIN lens/fiber 610 has a thickness of 0.1200 mm defined by the distance between an end 640 of lens 610 and an opposite end 645 of lens 610 and spacer 630 has a thickness of 0.6000 mm defined by the distance between end 650 and an opposite end 655 of spacer 630. As shown in FIG. 6, end 640 directly engages end 655 and end 650 is positioned opposite end 645. Table 4B lists the resulting beam characteristics of probe 600. As shown in Table 4B, the configuration of probe 600 of FIG. 6 results in a long focal length with a short working distance, achieving close to the desired optical performance. However, issues arise from manufacturing with tight tolerances of the GRIN lens and spacer (less than +/−1.2 micron for the GRIN and less than +/−10 micron for the spacer).

An optical probe must be specifically manufactured to conform to the optical parameters discussed above to be effective for esophageal imaging. Indeed, esophageal imaging requires probes of specific design to properly image into surrounding tissue T. When using an optical probe for esophageal imaging, a short working distance with large confocal parameter is required. In all of the prior attempts the manufacturing tolerances are extremely tight and do not allow for the production of an optical probe that is simple to manufacture and conforms to the optical parameters required in esophageal imaging.

The claimed optical probes differ from the experimental designs discussed above in that a spacer is positioned between a GRIN lens and a prism in each of the optical probes. This design allows for a probe with aberration correction of the outer sheath that is inexpensive to manufacture, possesses much lower tolerances to the manufacturing specifications, and has a short working distance with a large confocal parameter. In some embodiments, the spacer is fused to at least one of the GRIN lens and the prism and the spacer is formed of fused silica.

Figure 7:
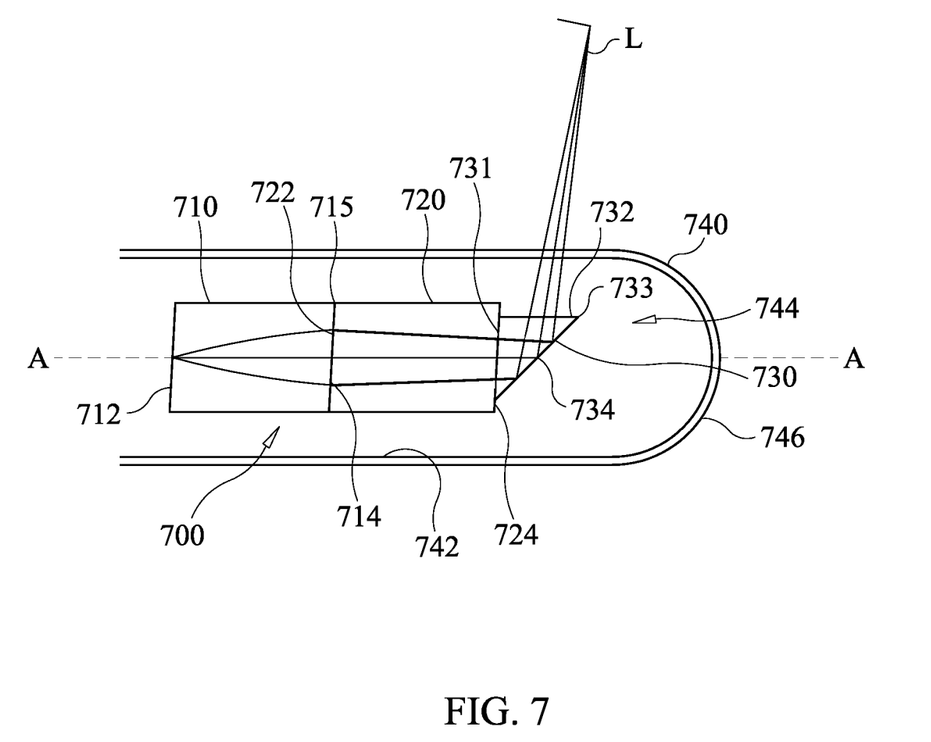
FIG. 7 is a side, cross-sectional view of an optical probe in accordance with the principles of the present disclosure.

FIG. 7 illustrates an optical probe 700 in accordance with the principles of the present disclosure. Probe 700 includes at least one lens, such as, for example, a GRIN lens 710 extending between an end 712 and an opposite end 714 along an axis A. One or more optical fibers (not shown) may be connected to end 712. The optical fiber(s) may be connected to a light source, such as, for example, a coherent light source. End 714 is directly connected to an end 722 of a spacer 720 that extends between end 722 and an opposite end 724 In some embodiments, end 714 is connected to end 722 by fusing end 714 to end 722 together or using an epoxy to glue the components together. End 712 is positioned opposite end 724 such that lens 710 and spacer 720 are coaxial. In one embodiment, an outer surface of lens 710 is flush with an outer surface of spacer 720 when spacer 720 is connected to lens 710. In some embodiments, lens 710 is a ball lens, conventional lens, or molded lens with a given thickness to perform similar to the GRIN lens. In some embodiments, probe 700 includes one lens 710 or a plurality of lenses 710. In some embodiments, spacer 720 is formed from a material that is different from a material from which lens 710 is formed. In some embodiments, spacer 720 comprises fused silica. In some embodiments, spacer 720 comprises glass. In some embodiments, spacer 720 comprises an air gap, plastic, index controlled liquid, or any other substance highly transmissive and close to the index of refraction of the prism and lens which aids in manufacturing.

In some embodiments, lens 710 is fused to spacer 720. In some embodiments, lens 710 is connected to spacer 720 using epoxy 715. In some embodiments, epoxy 715 is selected to match closely to the index of refraction of the adjoining components to reduce Fresnel Reflection and maintain high transmission In some embodiments, epoxy 715 is an epoxy manufactured by optical adhesive manufactured by Norland Products Inc. or an EpoTek optical adhesive. In some embodiments, epoxy 715 closely matches the index of refraction of at least one of lens 710 and spacer 720. In one embodiment, the index of refraction of GRIN lens 710 is 1.52 and the index of refraction spacer 720 is 1.467. In some embodiments, epoxy 715 is curable by, for example, UV light. In some embodiments, lens 710 is connected to spacer 720 by frictional engagement, threaded engagement, mutual grooves, screws, adhesive, nails, barbs and/or raised element.

Positioned after spacer 720 is a prism 730. Prism 730 extends between an end 731 and an opposite end 733 along axis A such that prism 730 is coaxial with lens 710 and spacer 720. End 731 directly connected to end 724 by fusing end 731 to end 724 or using an epoxy to glue end 731 to end 724. In one embodiment, prism 730 is a mirror. In some embodiments, prism 730 comprises glass, plastic or fluorite. In some embodiments, prism 730 is, an Amici roof prism, or a Bauernfeind prism.

In some embodiments, prism 730 is fused to spacer 720. In some embodiments, prism 730 is connected to spacer 720 using epoxy 725. In some embodiments, epoxy 725 is selected to match closely to the index of refraction of the adjoining components to reduce Fresnel Reflection and maintain high transmission. That is, in some embodiments, epoxy 725 closely matches the index of refraction of at least one of spacer 720 and prism 730. In some embodiments, epoxy 725 is curable by, for example, UV light and/or heat. In some embodiments, spacer 720 is connected to prism 730 by frictional engagement, threaded engagement, mutual grooves, screws, adhesive, nails, barbs and/or raised element.

In one embodiment, lens 710 has a thickness defined by the distance between ends 712, 714 that is equivalent or approximately equivalent to (i.e. within 0 to 1%) a thickness of spacer 720, the thickness of spacer 720 being defined by the distance between ends 722, 724. In one embodiment, the thickness of lens 710 is greater than the thickness of spacer 720. In one embodiment, the thickness of spacer 720 is between about 50% to about 99% of the thickness of lens. In one embodiment, the thickness of spacer 720 is between about 75% to about 95% of the thickness of lens. In one embodiment, the thickness of spacer 720 is between about 85% to about 90% of the thickness of lens. In one embodiment, the thickness of lens 710 is less than the thickness of spacer 720. In some embodiments, lens 710 has a thickness between about 0.5 mm and about 5.0 mm and spacer 720 has a thickness between about 0.5 mm and about 5.0 mm.

A sheath 740 is also illustrated in FIG. 7. Sheath 740 includes an inner surface 742 defining a passageway 744 having lens 710, spacer 720 and prism 730 removably disposed therein such that lens 710, spacer 720 and prism 730 are rotatable within passageway 744. An end 746 of sheath 740 is closed so as to define a blunt tip. In some embodiments, at least one of lens 710, spacer 720 and prism 730 are fixed to sheath 740 by, for example, adhesive applied to an outer surface of lens 710, spacer 720 and/or prism 730 and surface 742. In some embodiments, sheath 740 comprises a flexible material. In some embodiments, sheath 740 comprises a rigid material. In some embodiments, sheath 740 comprises at least one section comprising a rigid material and at least one section that comprises a flexible material, the section(s) that comprise(s) the rigid material being distinct from the section(s) that comprise(s) the flexible material. In some embodiments, sheath 740 comprises a non-metal material. In some embodiments, sheath 740 is transparent. In some embodiments, sheath 740 is not transparent and includes one or more openings extending through surface 742 and an outer surface of sheath 740 configured for passage of optical energy, such as, for example, a light path.

Table 5A lists the specifications of the components of one embodiment of optical probe 700. As shown in Table 5A, in one embodiment of optical probe 700, GRIN lens 710 has a thickness of 3.0000 mm defined by the distance between ends 712, 714 and spacer 720 has a thickness of 2.6500 mm defined by the distance between ends 722, 724. The combined length of GRIN lens 710 and spacer 720 of 5.6500 mm is prohibitive in most applications since a long optical probe would damage surrounding tissue in tight locations, e.g. an artery. However, esophageal imaging allows for a probe having a greater length thus permitting the dimensions associated with a probe in accordance with the principles of the present disclosure.

Table 5B lists the resulting beam characteristics of the embodiment of probe 700 detailed in Table 5A. As shown in Table 5B, the configuration of probe 700 of FIG. 7 results in a large waist and a short working distance with a large confocal parameter. For example, the beam of the embodiment of probe 700 detailed in Table 5A yields a waist $1/e^2$ radius of 20.6 μm-20.0 μm, a working distance of 1.6 mm after sheath 740, and a confocal parameter of 2.0 mm in air (2.8 mm in tissue). The confocal parameter allows for imaging 2-3 mm deep into surrounding tissue when optical probe 700 is positioned within the anatomy of a patient, such as, for example, in the patient's esophagus. The resulting Rayleigh Range Rz is approximately 1.0 mm in air (1.4 mm in tissue).

Adjustments to the lengths of GRIN lens 710 and spacer 720 within the parameters discussed above allow for adjustment with very tight tolerances to the spot size (i.e. waist) and working distance. Increasing the thickness of GRIN lens 710 decreases the spot size and a decreasing the thickness of GRIN lens 710 increases the spot size. Increasing the thickness of spacer 720 decreases the working distance and a decreasing the thickness of spacer 720 increases the working distance. The tolerances are proportional to the thickness of GRIN lens 710 and thus may be adjusted for by keeping GRIN lens 710 within a preferred range of +/−1% effective focal length from nominal. In one embodiment, lens 710 has a thickness of 3.000 mm will have +/−30 μm).

Problems with aberrations and back reflection are typical in conventional probes. This typically occurs when mating and other surfaces are perpendicular to a light path. Conventional optical probes force this correction by maintaining tight tolerances to component design, while maintaining the perpendicular surfaces. This is usual in the designing of conventional optical probes because the assembly of perpendicular surfaces makes for easier manufacturing.

Figure 8:
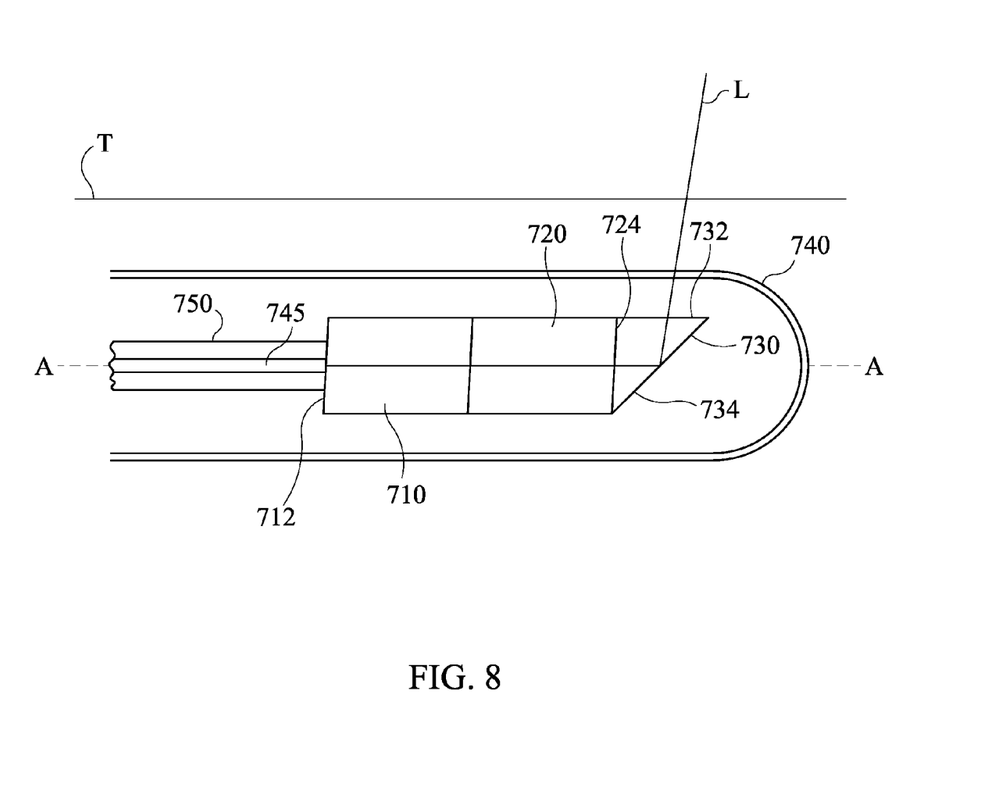
FIG. 8 is a side, cross-sectional view of an optical probe in accordance with the principles of the present disclosure.

In order to address the aberrations and back reflection issues, optical probe 700 has been designed such that mating surfaces of probe 700, such as, for example, end surfaces defined by ends 710, 712, 722, 724, 731 are not perpendicular to a light path L after light path L reflects from or pass through prism 730. In some embodiments, surfaces of one or more optical fibers 745, end surfaces of ends 712, 714 of GRIN lens 710, end surfaces of ends 722, 724 of spacer 720 and upper and lower surfaces 732, 734 of prism 730 are all off perpendicular to light path L. Optical fiber(s) 745 is/are connected to end 712. In some embodiments, optical fiber(s) 745 are surrounded by a casing 750. In some embodiments, end surfaces of ends 710, 712, 722, 724 are all angled between about 1 and about 10 degrees relative to light path L. In one embodiment, end surfaces of ends 710, 712, 722, 724 are all angled relative to axis A such that none of ends 710, 712, 722, 724 are perpendicular to axis A. In some embodiments, ends 710, 712, 722, 724 are angled 4 degrees relative to light path L. In some embodiments, prism 730 is a cylindrical right angle prism. Any gaps or defects that may exist between components of probe 700, such as, for example, between lens 710 and spacer 720 and/or between spacer 720 and prism 730 are corrected for by epoxies, such as, for example, epoxy 715 and/or epoxy 725, between the mating surfaces.

The present disclosure has been described herein in connection with an optical imaging system including an OCT probe. Other applications are contemplated. For example, it is envisioned that the devices disclosed herein may be used for imaging any portion of a patient's anatomy, such as, for example, a patient's esophagus, lungs, liver and/or portions related to the patient's esophagus, lungs or liver, such as, for example, bile ducts.

TABLE 1A

Lens Data Manager

| Surface # | Surface Name | Surface Type | Y Radius | X Radius | Thickness | Glass | Refract Mode | Y Semi-Aperture | X Semi-Aperture | Non-Centered Data |
|---|---|---|---|---|---|---|---|---|---|---|
| Object | | Sphere | Infinity | Infinity | 0.0000 | | Refract | | | |
| 1 | | Sphere | Infinity | Infinity | 0.0000 | | Refract | 0.0000 | 0.0000 | |
| Stop | SMF26_EN | Sphere | Infinity | Infinity | 0.0100 | SILICA_S | Refract | 0.1000 | 0.1000 | |
| 3 | Spacer | Sphere | Infinity | Infinity | 0.0000 | SILICA_S | Refract | 0.5000 | 0.5000 | Decenter & Return |
| 4 | Grin Len | Sphere | Infinity | Infinity | 3.2810 | SLW10_NS | Refract | 0.3000 | 0.3000 | Decenter & Return |
| 5 | Dummy Su | Sphere | Infinity | Infinity | 0.0000 | | Refract | 0.5000 | 0.5000 | Decenter & Return |
| 6 | Right An | Sphere | Infinity | Infinity | 0.3550 | SILICA_S | Refract | 0.3550 | 0.3550 | Decenter & Return |
| 7 | Right An | Sphere | Infinity | Infinity | −0.3550 | SILICA_S | Reflect | 0.5020 | 0.3550 | Decenter & Bend |
| 8 | | X Toroid | Infinity | 3.8480 | −0.3450 | | Refract | 0.3550 | 0.3550 | Decenter & Bend |
| 9 | Inner_Tu | X Toroid | Infinity | 0.7000 | −0.2000 | Vestami | Refract | 0.3550 | 0.5000 | Decenter & Bend |
| 10 | | X Toroid | Infinity | 0.9000 | −1.6000 | | Refract | 0.3550 | 0.5000 | |
| 11 | | Sphere | Infinity | Infinity | 0.0000 | | Refract | 0.3917 | 0.3917 | |
| Image | | Sphere | Infinity | Infinity | 0.0000 | | Refract | 0.3805 | 0.3805 | Decenter & Return |

TABLE 1B

Gaussian Beam Propagation
Zemax Optical Probe Converted
WAVELENGTH = 1300.0 nm
Dimensions = Millimeters
POSITION
FIELD POSITION = (0.00, 0.00)

| | PROPAGATION DISTANCE | BEAM RADIUS ON SURFACE | | BEAM ORIENTATION | WAVEFRONT RADIUS OF CURVATURE BEFORE REFRACTION | | PHASE ORIENTATION | WAIST RADIUS BEFORE REFRACTION | | |
|---|---|---|---|---|---|---|---|---|---|---|
| SUR | TO NEXT SURFACE | X | Y | (DEGREES) | X | Y | (DEGREES) | X | Y | DISTANCE |
| OBJ | 0.0000 | 0.0046 | 0.0046 | 0.0 | INF | INF | 0.0 | 0.0046 | 0.0046 | −0.0000 |
| 1 | 0.0000 | 0.0046 | 0.0046 | 0.0 | INF | INF | 0.0 | 0.0046 | 0.0046 | −0.0000 |
| 2 | 0.0100 | 0.0046 | 0.0046 | 0.0 | INF | INF | 0.0 | 0.0046 | 0.0046 | −0.0000 |

TABLE 1B-continued

Gaussian Beam Propagation
Zemax Optical Probe Converted
WAVELENGTH = 1300.0 nm
Dimensions = Millimeters
POSITION
FIELD POSITION = (0.00, 0.00)

| SUR | PROPAGATION DISTANCE TO NEXT SURFACE | BEAM RADIUS ON SURFACE X | Y | BEAM ORIENTATION (DEGREES) | WAVEFRONT RADIUS OF CURVATURE BEFORE REFRACTION X | Y | PHASE ORIENTATION (DEGREES) | WAIST RADIUS BEFORE REFRACTION X | Y | DISTANCE |
|---|---|---|---|---|---|---|---|---|---|---|
| 3 | 0.0000 | 0.0046 | 0.0047 | 0.0 | −0.5574 | −0.5574 | 0.0 | 0.0046 | 0.0046 | 0.0000 |
| 4 | 3.2803 | 0.0046 | 0.0047 | 0.0 | −0.5574 | −0.5574 | 0.0 | 0.0046 | 0.0046 | 0.0000 |
| 5 | 0.0000 | 0.0874 | 0.0876 | 0.0 | 4.0374 | 4.0366 | 0.0 | 0.0119 | 0.0119 | −3.9627 |
| 6 | 0.3482 | 0.0874 | 0.0876 | 0.0 | 2.5367 | 2.5211 | 0.0 | 0.0119 | 0.0119 | −2.4898 |
| 7 | −0.3623 | 0.0791 | 0.1219 | 0.0 | 3.3295 | 3.3323 | 0.0 | 0.0119 | 0.0119 | −3.2543 |
| 8 | −0.3508 | 0.0705 | 0.0707 | 0.0 | −2.9766 | −2.9795 | 0.0 | 0.0119 | 0.0119 | 2.8920 |
| 9 | −0.2015 | 0.0557 | 0.0592 | 0.0 | −1.3168 | −1.7067 | 0.0 | 0.0096 | 0.0119 | 1.2772 |
| 10 | −1.6277 | 0.0554 | 0.0547 | 0.0 | −40.8499 | −2.4153 | 0.0 | 0.0534 | 0.0120 | 2.8127 |
| 11 | 0.0663 | 0.0123 | 0.0129 | 0.0 | 3.8118 | 1.0606 | 0.0 | 0.0122 | 0.0119 | −0.0343 |
| IMG | | 0.0123 | 0.0120 | 0.0 | −4.0899 | 2.0701 | 0.0 | 0.0122 | 0.0119 | 0.0319 |

TABLE 2A

| Surface # | Surface Name | Surface Type | Y Radius | X Radius | Thickness | Glass | Refract Mode | Y Semi-Aperture | X Semi-Aperture | Non-Centered Data |
|---|---|---|---|---|---|---|---|---|---|---|
| Object | | Sphere | Infinity | Infinity | 0.0000 | | Refract | | | |
| 1 | | Sphere | Infinity | Infinity | 0.0000 | | Refract | 0.0000 | 0.0000 | |
| Stop | SMF28_En | Sphere | Infinity | Infinity | 0.1000 | SILICA_S | Refract | 0.1000 | 0.1000 | |
| 3 | Spacer | Sphere | Infinity | Infinity | 1.0000 | SILICA_S | Refract | 0.5000 | 0.5000 | Decenter & Return |
| 4 | Grin Len | Sphere | Infinity | Infinity | 3.0000 | SLO10_NS | Refract | 0.3000 | 0.3000 | Decenter & Return |
| 5 | Dummy Su | Sphere | Infinity | Infinity | 0.0000 | | Refract | 0.5000 | 0.5000 | Decenter & Return |
| 6 | Right An | Sphere | Infinity | Infinity | 0.3550 | SILICA_S | Refract | 0.3550 | 0.3550 | Decenter & Return |
| 7 | Right An | Sphere | Infinity | Infinity | −0.3550 | SILICA_S | Reflect | 0.5020 | 0.5020 | Becenter & Bend |
| 8 | | X Toroid | Infinity | 3.8480 | −0.3450 | | Refract | 0.3550 | 0.3550 | Becenter & Bend |
| 9 | Inner_Tu | X Toroid | Infinity | 0.7000 | −0.2000 | Vestami | Refract | 0.5000 | 0.5000 | Becenter & Bend |
| 10 | | X Toroid | Infinity | 0.9000 | −0.0500 | | Refract | 0.5000 | 0.5000 | |
| 11 | | Sphere | Infinity | Infinity | 0.0000 | | Refract | 0.1008 | 0.1008 | |
| Image | | Sphere | Infinity | Infinity | 0.0000 | | Refract | 0.0965 | 0.0965 | Decenter |

TABLE 2B

Gaussian Beam Propagation
WAVELENGTH = 1300.0 NM
Dimensions = Millimeters
POSITION
FIELD POSITION = (0.00, 0.00)

| SUR | PROPAGATION DISTANCE TO NEXT SURFACE | BEAM RADIUS ON SURFACE X | Y | BEAM ORIENTATION (DEGREES) | WAVEFRONT RADIUS OF CURVATURE BEFORE REFRACTION X | Y | PHASE ORIENTATION (DEGREES) | WAIST RADIUS BEFORE REFRACTION X | Y | DISTANCE X |
|---|---|---|---|---|---|---|---|---|---|---|
| OBJ | 0.0000 | 0.0046 | 0.0046 | 0.0 | INF | INF | 0.0 | 0.0046 | 0.0046 | −0.0000 |
| 1 | 0.0000 | 0.0046 | 0.0046 | 0.0 | INF | INF | 0.0 | 0.0046 | 0.0046 | −0.0000 |
| 2 | 0.0100 | 0.0046 | 0.0046 | 0.0 | INF | INF | 0.0 | 0.0046 | 0.0046 | −0.0000 |
| 3 | 1.0000 | 0.0046 | 0.0047 | 0.0 | −0.5574 | −0.5574 | 0.0 | 0.0046 | 0.0046 | 0.0100 |
| 4 | 2.9993 | 0.0630 | 0.0631 | 0.0 | −1.0154 | −1.0154 | 0.0 | 0.0046 | 0.0046 | 1.0100 |
| 5 | 0.0000 | 0.0787 | 0.0789 | 0.0 | 1.6102 | 1.6088 | 0.0 | 0.0053 | 0.0053 | −1.6029 |

TABLE 2B-continued

Gaussian Beam Propagation
WAVELENGTH = 1300.0 NM
Dimensions = Millimeters
POSITION
FIELD POSITION = (0.00, 0.00)

| SUR | PROPAGATION DISTANCE TO NEXT SURFACE | BEAM RADIUS ON SURFACE | | BEAM ORIENTATION (DEGREES) | WAVEFRONT RADIUS OF CURVATURE BEFORE REFRACTION | | PHASE ORIENTATION (DEGREES) | WAIST RADIUS BEFORE REFRACTION | | DISTANCE X |
|---|---|---|---|---|---|---|---|---|---|---|
| | | X | Y | | X | Y | | X | Y | |
| 6 | 0.3472 | 0.0787 | 0.0789 | 0.0 | 1.0117 | 1.0038 | 0.0 | 0.0053 | 0.0053 | −1.0071 |
| 7 | −0.3633 | 0.0600 | 0.0923 | 0.0 | 1.1188 | 1.1172 | 0.0 | 0.0053 | 0.0053 | −1.1100 |
| 8 | −0.3506 | 0.406 | 0.0406 | 0.0 | −0.7597 | −0.7282 | 0.0 | 0.0053 | 0.0053 | 0.7468 |
| 9 | −0.2015 | 0.0124 | 0.0139 | 0.0 | −0.1635 | −0.1894 | 0.0 | 0.0050 | 0.0053 | 0.1367 |
| 10 | −0.0509 | 0.0056 | 0.0059 | 0.0 | −0.6310 | −0.2849 | 0.0 | 0.0055 | 0.0053 | 0.0203 |
| 11 | 0.0160 | 0.0061 | 0.0057 | 0.0 | 0.1898 | 0.2313 | 0.0 | 0.0055 | 0.0053 | −0.0344 |
| IMG | | 0.0057 | 0.0053 | 0.0 | 0.3097 | 0.7957 | 0.0 | 0.0055 | 0.0053 | −0.0183 |

TABLE 3A

Lens Data Manager

| Surface # | Surface Name | Surface Type | Y Radius | X Radius | Thickness | Glass | Refract Mode | Y Semi-Aperture | X Semi-Aperture | Non-Centered Data |
|---|---|---|---|---|---|---|---|---|---|---|
| Object | | Sphere | Infinity | Infinity | 0.0000 | | Refract | | | |
| 1 | | Sphere | Infinity | Infinity | 0.0000 | | Refract | 0.0000 | 0.0000 | |
| Stop | SMF28_EN | Sphere | Infinity | Infinity | 0.0100 | SILICA_S | Refract | 0.1000 | 0.1000 | |
| 3 | Spacer | Sphere | Infinity | Infinity | 0.0000 | SILICA_S | Refract | 0.5000 | 0.5000 | Decenter & Return |
| 4 | Grin Len | Sphere | Infinity | Infinity | 3.9200 | SLW10_NS | Refract | 0.3000 | 0.3000 | Decenter & Return |
| 5 | Dummy Su | Sphere | Infinity | Infinity | 0.0000 | | Refract | 0.5000 | 0.5000 | Decenter & Return |
| 6 | Right An | Sphere | Infinity | Infinity | 0.3550 | SILICA_S | Refract | 0.3550 | 0.3550 | Decenter & Return |
| 7 | Right An | Sphere | Infinity | Infinity | −0.3550 | SILICA_S | Reflect | 0.5020 | 0.3550 | Decenter & Bend |
| 8 | | X Toroid | Infinity | 3.8480 | −0.3450 | | Refract | 0.3550 | 0.3550 | Decenter & Bend |
| 9 | Inner_Tu | X Toroid | Infinity | 0.7000 | −0.2000 | Vestami | Refract | 0.5000 | 0.5000 | Decenter & Bend |
| 10 | | X Toroid | Infinity | 0.9000 | −1.1000 | | Refract | 0.5000 | 0.5000 | |
| 11 | | Sphere | Infinity | Infinity | 0.0000 | | Refract | 0.1145 | 0.1145 | |
| Image | | Sphere | Infinity | Infinity | 0.0000 | | Refract | 0.1101 | 0.1101 | Decenter & Return |

TABLE 3B

Gaussian Beam Propagation
WAVELENGTH = 1300.0 NM
Dimensions = Millimeters
POSITION
FIELD POSITION = (0.00, 0.00)

| SUR | PROPAGATION DISTANCE TO NEXT SURFACE | BEAM RADIUS ON SURFACE | | BEAM ORIENTATION (DEGREES) | WAVEFRONT RADIUS OF CURVATURE BEFORE REFRACTION | | PHASE ORIENTATION (DEGREES) | WAIST RADIUS BEFORE REFRACTION | | DISTANCE X |
|---|---|---|---|---|---|---|---|---|---|---|
| | | X | Y | | X | Y | | X | Y | |
| OBJ | 0.0000 | 0.0046 | 0.0046 | 0.0 | INF | INF | 0.0 | 0.0046 | 0.0046 | −0.0000 |
| 1 | 0.0000 | 0.0046 | 0.0046 | 0.0 | INF | INF | 0.0 | 0.0046 | 0.0046 | −0.0000 |
| 2 | 0.0100 | 0.0046 | 0.0046 | 0.0 | INF | INF | 0.0 | 0.0046 | 0.0046 | −0.0000 |
| 3 | 0.0000 | 0.0046 | 0.0047 | 0.0 | −0.5574 | −0.5574 | 0.0 | 0.0046 | 0.0046 | 0.0100 |
| 4 | 3.9195 | 0.0046 | 0.0047 | 0.0 | −0.5574 | −0.5574 | 0.0 | 0.0046 | 0.0046 | 0.0100 |
| 5 | 0.0000 | 0.0677 | 0.0678 | 0.0 | 1.7153 | 1.7150 | 0.0 | 0.0066 | 0.0066 | −1.6992 |
| 6 | 0.3516 | 0.0677 | 0.0678 | 0.0 | 1.0777 | 1.0691 | 0.0 | 0.0066 | 0.0065 | −1.0676 |
| 7 | −0.3591 | 0.0524 | 0.0809 | 0.0 | 1.2121 | 1.2111 | 0.0 | 0.0066 | 0.0066 | −1.1931 |

TABLE 3B-continued

Gaussian Beam Propagation
WAVELENGTH = 1300.0 NM
Dimensions = Millimeters
POSITION
FIELD POSITION = (0.00, 0.00)

| SUR | PROPAGATION DISTANCE TO NEXT SURFACE | BEAM RADIUS ON SURFACE X | Y | BEAM ORIENTATION (DEGREES) | WAVEFRONT RADIUS OF CURVATURE BEFORE REFRACTION X | Y | PHASE ORIENTATION (DEGREES) | WAIST RADIUS BEFORE REFRACTION X | Y | DISTANCE X |
|---|---|---|---|---|---|---|---|---|---|---|
| 8 | −0.3513 | 0.369 | 0.0370 | 0.0 | −0.8612 | −0.8603 | 0.0 | 0.0066 | 0.0066 | 0.8341 |
| 9 | −0.2016 | 0.0142 | 0.0157 | 0.0 | −0.2338 | −0.2687 | 0.0 | 0.0061 | 0.0065 | 0.1899 |
| 10 | −0.1018 | 0.0084 | 0.0088 | 0.0 | −0.4062 | −0.3198 | 0.0 | 0.0071 | 0.0066 | 0.1142 |
| 11 | 0.0190 | 0.0069 | 0.0067 | 0.0 | 0.631 | 0.8110 | 0.0 | 0.0068 | 0.0065 | −0.0214 |
| IMG | | 0.0068 | 0.0065 | 0.0 | 5.0095 | −1.9007 | 0.0 | 0.0068 | 0.0065 | −0.0024 |

TABLE 4A

Lens Data Manager

| Surface # | Surface Name | Surface Type | Y Radius | X Radius | Thickness | Glass | Refract Mode | Y Semi-Aperture | X Semi-Aperture | Non-Centered Data |
|---|---|---|---|---|---|---|---|---|---|---|
| Object | | Sphere | Infinity | Infinity | 0.0000 | | Refract | | | |
| 1 | | Sphere | Infinity | Infinity | 0.0000 | | Refract | 0.0000 | 0.0000 | |
| Stop | SMF28_EN | Sphere | Infinity | Infinity | 0.0100 | SILICA_S | Refract | 0.1000 | 0.1000 | |
| 3 | Spacer | Sphere | Infinity | Infinity | 0.6000 | SILICA_S | Refract | 0.1000 | 0.1000 | Decenter & Return |
| 4 | Grin Len | Sphere | Infinity | Infinity | 0.1200 | SLW10_NS | Refract | 0.1000 | 0.1000 | Decenter & Return |
| 5 | Dummy Su | Sphere | Infinity | Infinity | 0.0000 | | Refract | 0.1000 | 0.1000 | Decenter & Return |
| 6 | Right An | Sphere | Infinity | Infinity | 0.3550 | SILICA_S | Refract | 0.3550 | 0.3550 | Decenter & Return |
| 7 | Right An | Sphere | Infinity | Infinity | −0.3550 | SILICA_S | Reflect | 0.5020 | 0.3550 | Decenter & Bend |
| 8 | | X Toroid | Infinity | 3.8480 | −0.3450 | | Refract | 0.3550 | 0.3550 | Decenter & Bend |
| 9 | Inner_Tu | X Toroid | Infinity | 0.7000 | −0.2000 | Vestami | Refract | 0.5000 | 0.5000 | Decenter & Bend |
| 10 | | X Toroid | Infinity | 0.9000 | −1.0000 | | Refract | 0.5000 | 0.5000 | |
| 11 | | Sphere | Infinity | Infinity | −1.0000 | | Refract | 0.2820 | 0.2820 | |
| Image | | Sphere | Infinity | Infinity | 0.0000 | | Refract | 0.4220 | 0.4220 | Decenter & Return |

TABLE 4B

Gaussian Beam Propagation
WAVELENGTH = 1300.0 NM
Dimensions = Millimeters
POSITION
FIELD POSITION = (0.00, 0.00)

| SUR | PROPAGATION DISTANCE TO NEXT SURFACE | BEAM RADIUS ON SURFACE X | Y | BEAM ORIENTATION (DEGREES) | WAVEFRONT RADIUS OF CURVATURE BEFORE REFRACTION X | Y | PHASE ORIENTATION (DEGREES) | WAIST RADIUS BEFORE REFRACTION X | Y | DISTANCE X |
|---|---|---|---|---|---|---|---|---|---|---|
| OBJ | 0.0000 | 0.0046 | 0.0046 | 0.0 | INF | INF | 0.0 | 0.0046 | 0.0046 | −0.0000 |
| 1 | 0.0000 | 0.0046 | 0.0046 | 0.0 | INF | INF | 0.0 | 0.0046 | 0.0046 | −0.0000 |
| 2 | 0.0100 | 0.0046 | 0.0046 | 0.0 | INF | INF | 0.0 | 0.0046 | 0.0046 | −0.0000 |
| 3 | 0.6000 | 0.0046 | 0.0047 | 0.0 | −0.5574 | −0.5574 | 0.0 | 0.0046 | 0.0046 | 0.0100 |
| 4 | 0.1200 | 0.0382 | 0.0383 | 0.0 | −0.6190 | −0.6190 | 0.0 | 0.0046 | 0.0046 | 0.6100 |
| 5 | 0.0000 | 0.0414 | 0.0415 | 0.0 | 4.8938 | 4.8855 | 0.0 | 0.0258 | 0.0257 | −2.9944 |
| 6 | 0.3548 | 0.0414 | 0.0415 | 0.0 | 3.2911 | 3.237 | 0.0 | 0.0258 | 0.0258 | −2.0137 |
| 7 | −0.3552 | 0.0383 | 0.0585 | 0.0 | 4.6633 | 4.6639 | 0.0 | 0.0258 | 0.0258 | −2.5589 |
| 8 | −0.3501 | 0.0355 | 0.0356 | 0.0 | −4.6473 | −4.6481 | 0.0 | 0.0258 | 0.0258 | 2.2037 |
| 9 | −0.2013 | 0.0305 | 0.0323 | 0.0 | −2.2565 | −3.3502 | 0.0 | 0.0216 | 0.0257 | 1.1224 |

TABLE 4B-continued

Gaussian Beam Propagation
WAVELENGTH = 1300.0 NM
Dimensions = Millimeters
POSITION
FIELD POSITION = (0.00, 0.00)

| SUR | PROPAGATION DISTANCE TO NEXT SURFACE | BEAM RADIUS ON SURFACE | | BEAM ORIENTATION (DEGREES) | WAVEFRONT RADIUS OF CURVATURE BEFORE REFRACTION | | PHASE ORIENTATION (DEGREES) | WAIST RADIUS BEFORE REFRACTION | | DISTANCE |
|---|---|---|---|---|---|---|---|---|---|---|
| | | X | Y | | X | Y | | X | Y | X |
| 10 | −1.0148 | 0.0317 | 0.0311 | 0.0 | 5.1654 | −5.3288 | 0.0 | 0.0259 | 0.0259 | −1.7080 |
| 11 | −0.9412 | 0.0266 | 0.0261 | 0.0 | −30.8349 | −143.9934 | 0.0 | 0.0256 | 0.0257 | 0.0939 |
| IMG | | 0.0296 | 0.0297 | 0.0 | 4.2543 | 3.6796 | 0.0 | 0.0256 | 0.0257 | −08473 |

TABLE 5A

Lens Data Manager

| Surface # | Surface Name | Surface Type | Y Radius | X Radius | Thickness | Glass | Refract Mode | Y Semi-Aperture | X Semi-Aperture | Non-Centered Data |
|---|---|---|---|---|---|---|---|---|---|---|
| Object | | Sphere | Infinity | Infinity | 0.0000 | | Refract | | | |
| 1 | | Sphere | Infinity | Infinity | 0.0000 | | Refract | 0.0000 | 0.0000 | |
| Stop | SMF28_EN | Sphere | Infinity | Infinity | 0.0100 | SILICA_S | Refract | 0.1000 | 0.1000 | |
| 3 | Spacer | Sphere | Infinity | Infinity | 0.0000 | SILICA_S | Refract | 0.5000 | 0.5000 | Decenter & Return |
| 4 | Grin Len | Sphere | Infinity | Infinity | 3.0000 | SLW10_NS | Refract | 0.3000 | 0.3000 | Decenter & Return |
| 5 | Dummy Su | Sphere | Infinity | Infinity | 2.6500 | SILICA_S | Refract | 0.1961 | 0.1961 | Decenter & Return |
| 6 | Right An | Sphere | Infinity | Infinity | 0.0000 | | Refract | 0.5000 | 0.5000 | Decenter & Return |
| 7 | Right An | Sphere | Infinity | Infinity | 0.3550 | SILICA_S | Refract | 0.3550 | 0.3550 | Decenter & Bend |
| 8 | Right An | Sphere | Infinity | | −0.3550 | SILICA_S | Reflect | 0.5020 | 0.3550 | Decenter & Bend |
| 9 | | X Toroid | Infinity | 3.8480 | −0.3450 | | Refract | 0.3550 | 0.3550 | Decenter & Bend |
| 10 | Inner_Tu | X Toroid | Infinity | 0.7000 | −0.2000 | Vestami | Refract | 0.5000 | 0.5000 | Decenter & Bend |
| 11 | | XToroid | Infinity | 0.9000 | −1.6000 | | Refract | 0.5000 | 0.5000 | |
| 12 | | Sphere | Infinity | Infinity | 0.0000 | | Refract | 0.4035 | 0.4035 | |
| Image | | Sphere | Infinity | Infinity | 0.0000 | | | 0.3968 | 0.3968 | Decenter & Return |

TABLE 5B

Gaussian Beam Propagation
WAVELENGTH = 1300.0 NM
Dimensions = Millimeters
POSITION
FIELD POSITION = (0.00, 0.00)

| SUR | PROPAGATION DISTANCE TO NEXT SURFACE | BEAM RADIUS ON SURFACE | | BEAM ORIENTATION (DEGREES) | WAVEFRONT RADIUS OF CURVATURE BEFORE REFRACTION | | PHASE ORIENTATION (DEGREES) | WAIST RADIUS BEFORE REFRACTION | | DISTANCE X |
|---|---|---|---|---|---|---|---|---|---|---|
| | | X | Y | | X | Y | | X | Y | |
| OBJ | 0.0000 | 0.0046 | 0.0046 | 0.0 | INF | INF | 0.0 | 0.0046 | 0.0046 | −0.0000 |
| 1 | 0.0000 | 0.0046 | 0.0046 | 0.0 | INF | INF | 0.0 | 0.0046 | 0.0046 | −0.0000 |
| 2 | 0.0100 | 0.0046 | 0.0046 | 0.0 | INF | INF | 0.0 | 0.0046 | 0.0046 | −0.0000 |
| 3 | 0.0000 | 0.0046 | 0.0047 | 0.0 | −0.5574 | −0.5574 | 0.0 | 0.0046 | 0.0046 | 0.0100 |
| 4 | 2.9993 | 0.0046 | 0.0047 | 0.0 | −0.5574 | −0.5574 | 0.0 | 0.0046 | 0.0046 | 0.0100 |
| 5 | 2.6517 | 0.0923 | 0.0925 | 0.0 | 7.2881 | 7.2860 | 0.0 | 0.0200 | 0.0201 | −6.9440 |
| 6 | 0.0000 | 0.0559 | 0.0562 | 0.0 | 4.2005 | 4.2188 | 0.0 | 0.0200 | 0.0201 | −3.6611 |
| 7 | 0.3718 | 0.0559 | 0.0562 | 0.0 | 2.9031 | 2.8961 | 0.0 | 0.0200 | 0.0200 | −2.5303 |
| 8 | −0.3386 | 0.0510 | 0.0786 | 0.0 | 3.8897 | 3.9083 | 0.0 | 0.0200 | 0.0201 | −3.2893 |
| 9 | −0.3522 | 0.0466 | 0.0468 | 0.0 | −3.6199 | −3.6389 | 0.0 | 0.0200 | 0.0201 | 2.9506 |

TABLE 5B-continued

Gaussian Beam Propagation
WAVELENGTH = 1300.0 NM
Dimensions = Millimeters
POSITION
FIELD POSITION = (0.00, 0.00)

| SUR | PROPAGATION DISTANCE TO NEXT SURFACE | BEAM RADIUS ON SURFACE X | BEAM RADIUS ON SURFACE Y | BEAM ORIENTATION (DEGREES) | WAVEFRONT RADIUS OF CURVATURE BEFORE REFRACTION X | WAVEFRONT RADIUS OF CURVATURE BEFORE REFRACTION Y | PHASE ORIENTATION (DEGREES) | WAIST RADIUS BEFORE REFRACTION X | WAIST RADIUS BEFORE REFRACTION Y | DISTANCE X |
|---|---|---|---|---|---|---|---|---|---|---|
| 10 | −0.2015 | 0.0383 | 0.0408 | 0.0 | −1.6448 | −2.2429 | 0.0 | 0.0161 | 0.0200 | 1.3527 |
| 11 | −1.6273 | 0.0389 | 0.0384 | 0.0 | 12.3893 | −3.2966 | 0.0 | 0.0356 | 0.0202 | −2.0236 |
| 12 | 0.0694 | 0.0206 | 0.0205 | 0.0 | −85.0579 | 12.3541 | 0.0 | 0.0206 | 0.0200 | 0.0123 |
| IMG | | 0.0206 | 0.0200 | 0.0 | −12.8684 | 126.6894 | 0.0 | 0.0206 | 0.0200 | 0.0816 |

While the preferred embodiments of the devices have been described in reference to the environment in which they were developed, they are merely illustrative of the principles of the devices. Modification or combinations of the above-described devices, other embodiments, configurations, and methods for carrying out the invention, and variations of aspects of the invention that are obvious to those of skill in the art are intended to be within the scope of the claims.

What is claimed is:

1. An optical probe, comprising:
   a lens extending along an axis between a first end and a second end, the first and second ends of the lens each defining an end surface that is not perpendicular to the axis;
   a spacer extending along the axis between a first end and a second end, the first end of the spacer being connected to the second end of the lens; and
   a prism connected to the second end of the spacer such that the prism is spaced apart from the lens by the spacer.

2. An optical probe as recited in claim 1, wherein the first end of the spacer is directly connected to the second end of the lens and the prism is directly connected to the second end of the spacer.

3. An optical probe as recited in claim 1, wherein:
   the spacer is connected to the lens using an epoxy having an index of refraction that matches an index of refraction of at least one of the spacer and the lens; and
   the spacer is connected to the prism using an epoxy having an index of refraction that matches an index of refraction of at least one of the spacer and the prism.

4. An optical probe as recited in claim 1, wherein the first end of the spacer is fused to the second end of the lens and the prism is fused to the second end of the spacer.

5. An optical probe as recited in claim 1, wherein the probe is configured to emit a light path from the prism such that the light path extends at angle between about 1 and about 10 degrees relative to a second axis that extends perpendicular to the axis.

6. An optical probe as recited in claim 1, wherein the probe is configured to emit a light path from the prism such that the light path extends at angle of 4 degrees relative to a second axis that extends perpendicular to the axis.

7. An optical probe as recited in claim 1, wherein:
   the probe is configured to emit a light path from the prism;
   the end surfaces of the lens are not perpendicular to the light path; and
   the first and second ends of the spacer define end surfaces that are not perpendicular to the light path or the axis.

8. An optical probe as recited in claim 1, wherein the lens is a gradient index lens and the spacer comprises glass.

9. An optical probe as recited in claim 1, wherein the spacer is fused to the lens and the prism and comprises fused silica.

10. An optical probe as recited in claim 1, wherein a thickness of the lens defined by a distance between the first and second ends of the lens is greater than a thickness of the spacer defined by a distance between the first and second ends of the spacer.

11. An optical probe as recited in claim 1, wherein a thickness of the lens defined by a distance between the first and second ends of the lens is 3.0 mm and a thickness of the spacer defined by a distance between the first and second ends of the spacer is 2.65 mm.

12. An optical probe as recited in claim 1, wherein a thickness of the lens defined by a distance between the first and second ends of the lens is equal to a thickness of the spacer defined by a distance between the first and second ends of the spacer.

13. An optical probe, comprising:
   a lens extending along an axis between a first end and a second end, the first and second ends of the lens each defining an end surface that is not perpendicular to the axis;
   one or more optical fibers connected to the first end of the lens;
   a spacer extending along the axis between a first end and a second end, the first end of the spacer being connected to the second end of the lens;
   a prism connected to the second end of the spacer such that the prism is spaced apart from the lens by the spacer; and
   a sheath including an inner surface defining a passageway having the lens, the spacer and the prism removably disposed therein.

14. An optical probe as recited in claim 13, wherein the sheath comprises a flexible material and is transparent.

15. An optical probe as recited in claim 13, wherein the sheath includes on or more openings extending through the inner surface and an outer surface of the sheath configured for passage of optical energy.

16. An optical probe as recited in claim 13, wherein the sheath includes a blunt tip.

17. An optical probe as recited in claim 13, wherein the spacer is connected to at least one of the lens and the prism using an epoxy having an index of refraction that matches an index of refraction of at least one of the spacer, the lens and the prism.

18. An optical probe as recited in claim 13, wherein:
the probe is configured to emit a light path from the prism;
the end surfaces of the lens are not perpendicular to the light path; and
the first and second ends of the spacer define end surfaces that are not perpendicular to the light path or the axis.

19. An optical probe, comprising:
a gradient index lens extending along an axis between a first end and a second end;
one or more optical fibers connected directly to the first end of the lens;
a spacer comprising fused silica extending along the axis between a first end and a second end, the first end of the spacer being connected directly to the second end of the lens by an epoxy having an index of refraction that matches an index of refraction of at least one of the spacer and the lens;
a prism connected directly to the second end of the spacer such that the prism is spaced apart from the lens by the spacer, the prism being connected to the spacer by an epoxy having an index of refraction that matches an index of refraction of at least one of the spacer and the prism; and
a flexible sheath including an inner surface defining a passageway having the lens, the spacer and the prism removably disposed therein,
wherein a thickness of the lens defined by a distance between the first and second ends of the lens is greater than a thickness of the spacer defined by a distance between the first and second ends of the spacer, and
wherein the probe is configured to emit a light path from the prism, the first and second ends of the lens defining end surfaces that are not perpendicular to the light path, and the first and second ends of the spacer defining end surfaces that are not perpendicular to the light path.

20. An optical probe as recited in claim 1, wherein the spacer comprises an index controlled liquid.

* * * * *